(12) United States Patent
Cao et al.

(10) Patent No.: US 6,582,906 B1
(45) Date of Patent: *Jun. 24, 2003

(54) PROPORTIONAL AMPLIFICATION OF NUCLEIC ACIDS

(75) Inventors: Yanxiang Cao, Palo Alto, CA (US); David J. Lockhart, Mountain View, CA (US); Rui Mei, Santa Clara, CA (US); Xing Su, Cupterino, CA (US)

(73) Assignee: Affymetrix, Inc., Santa Clara, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/285,658

(22) Filed: Apr. 5, 1999

(51) Int. Cl.$^7$ .......................... C12Q 1/68; C12Q 19/34
(52) U.S. Cl. ........................ 435/6; 435/91.2; 435/91.51
(58) Field of Search .................... 435/91.2, 6, 91.51

(56) References Cited

U.S. PATENT DOCUMENTS

| | | | |
|---|---|---|---|
| 5,399,491 A | 3/1995 | Kacian et al. | 435/91.21 |
| 5,409,818 A | 4/1995 | Davey et al. | 435/6 |
| 5,437,990 A | 8/1995 | Burg et al. | 435/91.2 |
| 5,445,934 A | 8/1995 | Fodor et al. | 435/6 |
| 5,514,545 A | 5/1996 | Eberwine | 435/6 |
| 5,545,522 A | 8/1996 | Van Gelder et al. | 435/6 |
| 5,554,516 A | 9/1996 | Kacian et al. | 435/91.21 |
| 5,554,517 A | 9/1996 | Davey et al. | 435/91.21 |
| 5,677,195 A | 10/1997 | Winkler et al. | 436/518 |
| 5,679,524 A | 10/1997 | Nikiforov et al. | 435/6 |
| 5,716,785 A | 2/1998 | Van Gelder et al. | 435/6 |
| 5,744,305 A | 4/1998 | Fodor et al. | 435/6 |
| 5,770,722 A | 6/1998 | Lockhart et al. | 536/25.3 |
| 5,891,636 A | 4/1999 | Van Gelder et al. | 435/6 |
| 5,932,451 A | 8/1999 | Wang et al. | 435/91.21 |
| 5,965,409 A | 10/1999 | Pardee et al. | 435/91.2 |
| 6,066,449 A | * 5/2000 | Ditkoff et al. | 435/6 |
| 6,066,457 A | * 5/2000 | Hampson et al. | 435/6 |
| 6,132,997 A | 10/2000 | Shannon | 435/91.21 |
| 6,203,984 B1 | 3/2001 | Hu et al. | 435/6 |

OTHER PUBLICATIONS

Kwoh et al. Transcription–based amplification system and detection of amplified human immunodeficiency virus type 1 with a bead–based sandwich hybridization format, Proc. Natl. Acad. Sci. USA, vol. 86, p. 1173–1174, 1989.*

Collins et al., "New Goals for the U.S. Human Genome Project: 1998–2003," *Science* 282:682–689 (Oct. 1998).

Eberwine et al., "Analysis of gene expression in single live neurones," *Proc. Natl. Acad. Sci.* 89:3010–3014 (Apr. 1992).

Lockhart et al., "Expression monitoring by hybridization to high–density oligonucleotide arrays," *Nature Biotech.* 14(13):1675–1680 (1996).

Winzeler et al. "Direct Allelic Variation scanning of the Yeast Genome," *Science* 281(5380):1101–1240 (1998).

Wodicka et al., "Genome–wide Expression monitoring in Saccharomyces cerevisiae," *Nature Biotech.* 15(13):1359–1367 (1997).

Zhang et al., "Whole genome amplification from a single cell: Implications for genetic analysis," *Proc. Natl. Acad. Sci.* 89:5847–5851 (Jul. 1992).

* cited by examiner

Primary Examiner—Ethan Whisenant
Assistant Examiner—Joyce Tung
(74) Attorney, Agent, or Firm—Sandra Wells; Philip L. McGarrigle

(57) ABSTRACT

The proportional amplification of nucleic acids can increase the amount of nucleic acids while preserving the relative abundance of the individual nucleic acid species, or portions thereof, in the original sample. A proportionally amplified nucleic acid preparation may be analyzed in a gene expression monitoring system, preferably involving a nucleic acid probe array.

22 Claims, 5 Drawing Sheets

Proportional Amplification of Complex Messenger RNA

PROPORTIONAL AMPLIFICATION OF NUCLEIC ACIDS

FIELD OF THE INVENTION

The present invention relates generally to the proportional amplification of nucleic acids. The methods of the present invention can facilitate the amplification of minute sample amounts of nucleic acids in a manner that may preserve the relative abundance of the individual nucleic acid species, or portions thereof, existing in the original sample.

BACKGROUND OF THE INVENTION

The isolation, characterization and manipulation of nucleic acids has numerous present or potential applications, including those in the basic research, diagnostic and forensic fields. Valuable information about gene expression in in vivo, in situ, and in vitro systems can be obtained by monitoring the abundance of the mRNA encoded by those genes. Methods involving the synthesis of cDNA from mRNA have also enhanced the study of gene expression, for example, by facilitating gene cloning and the production of desired recombinant proteins.

With existing methods for the study or use of MRNA and cDNA, one problematic scenario can arise where the sample size is small, or the relative abundance of an individual MRNA or cDNA species in a sample is low. In such situations, where the availability or accessibility of the desired mRNA or cDNA is compromised (or their amounts are otherwise limited), the lower limits of monitoring or manipulation systems may be exceeded, thus leaving the desired MRNA or cDNA undetected, unrecoverable or unworkable. Therefore, the amplification of such MRNA and cDNA is an important molecular biology methodology, with particular significance in facilitating the detection and study of a broader range of mRNA molecules, and the isolation and manipulation of mRNA available in only minute quantities.

Although methods exist for the amplification of nucleic acids, they generally suffer from a phenomenon known as biased amplification. In these cases, the amplified population does not proportionally represent the population of nucleic acid species existing in the original sample. This drawback may preclude meaningful or reliable conclusions regarding the absolute amount or relative abundance of a desired nucleic acid species in the tested sample.

One common problem encountered by past amplification methods is the preference for the amplification of shorter nucleic acid templates. The enzymes responsible for the production of complements or copies of the nucleic acid templates (e.g., DNA and RNA polymerases, or reverse transcriptases) achieve such synthesis through a sequential, oriented process, whether 5' to 3' or 3' to 5'. The probability that such an enzyme will complete a copying event thus may be greater with nucleic acid templates of shorter length. Accordingly, in a sample population containing nucleic acid templates of variable lengths, longer templates may be less likely than shorter templates to be amplified in complete, full-length form. This can result in a bias in the amplified population in favor of nucleotide sequences proximal to the 3' poly(A) tail of MRNA, for example, a phenomenon known as 3'-sequence bias.

The synthesis of longer templates can also be difficult or less efficient due to interference from secondary and tertiary structure in the template. For example, with respect to nucleic acid amplification based on polymerase chain reaction (PCR) methodologies, longer templates in a sample may be under-represented in the amplified product if respective primers cannot anneal to begin another round of copying because the first round did not proceed to completion. Other potential sources of bias can reflect relative differences between longer and shorter templates. For example, longer templates may (i) not denature sufficiently, or (ii) have a greater likelihood of mismatches, and thus error propagation through amplification, but (iii) have an ability to anneal more easily.

Known nucleic acid amplification methods have not successfully overcome such problems with biased amplification. U.S. Pat. No. 5,716,785, for example, describes an amplification system involving the production of antisense RNA from cDNA synthesized from a MRNA population. The methodology set forth in the '785 patent also results in 3'-sequence biased amplification.

The foregoing shows a need for methods and products involving the amplification of nucleic acids in a manner to facilitate the preservation of the relative abundance of the individual nucleic acid species existing in the original sample.

SUMMARY OF THE INVENTION

An objective of the present invention is therefore the proportional amplification of nucleic acids.

In accomplishing these and other objectives, the present invention preferably provides methods for the proportional amplification of nucleic acids that may comprise creating fragments of a single-stranded DNA population, synthesizing double-stranded DNA from the fragments of a single-stranded DNA population, and producing multiple copies of sense RNA from the double-stranded DNA. In another preferred embodiment, the present invention provides methods for the proportional amplification of nucleic acid that may comprise creating fragments of a double-stranded DNA population, and synthesizing multiple copies of the fragments of a double-stranded DNA population. In yet another preferred embodiment, the present invention provides methods for the proportional amplification of nucleic acid that may comprise synthesizing multiple copies of a double-stranded DNA population, and creating fragments of the multiple copies of a double-stranded DNA population.

In addition, the present invention preferably provides methods for the proportional amplification of nucleic acid that may further comprise labeling the multiple copies of the fragments of a double-stranded DNA population, or producing multiple copies of RNA from the multiple copies of the fragments of a double-stranded DNA population, or producing multiple copies of RNA from the fragments of the multiple copies of a double-stranded DNA population.

In a preferred embodiment, the present invention provides methods in which the single-stranded or double-stranded DNA population may be produced from a nucleic acid population selected from the group consisting of one or more of the following: genomic DNA, cDNA, total RNA, poly(A)$^+$ RNA, and oligonucleotides. In a preferred embodiment, the poly(A)$^+$ RNA may be mRNA.

The present invention also preferably provides methods, which may further comprise making fragments of the RNA or DNA obtained by the described proportional amplification methods, contacting the fragments with a solid support comprising nucleic acid probes, and detecting the presence or absence of hybridization of the fragments to the nucleic acid probes on the solid support. In a preferred embodiment, the solid support, which may comprise nucleic acid probes, can be selected from the group consisting of a nucleic acid probe array, a membrane blot, a microwell, a bead, and a sample tube.

In another embodiment, the present invention preferably provides methods in which the described steps are repeated once or multiple times. For example, in a preferred embodiment, the present invention may further comprise creating an additional set of single-stranded DNA from the multiple copies of sense RNA, synthesizing an additional set of double-stranded DNA from the additional set of single-stranded DNA, and producing an additional set of multiple copies of sense RNA from the additional set of double-stranded DNA.

In a preferred embodiment, the fragments of a single-stranded DNA population of the present invention may be from about 30 nucleotides to about 3,000 nucleotides in length. In another, these fragments may be from about 30 nucleotides to about 750 nucleotides in length. In yet another, these fragments may be from about 30 nucleotides to about 150 nucleotides in length.

The present invention may preferably provide methods wherein the RNA may be isolated from an eukaryotic cell or tissue, mammalian cell or tissue, or human cell or tissue. In a preferred embodiment, the RNA may be isolated from a source selected from the group consisting of dissected tissue, microdissected tissue, a tissue subregion, a tissue biopsy sample, a cell sorted population, a cell culture, and a single cell. In another preferred embodiment, the RNA may be isolated from a cell or tissue source selected from the group consisting of brain, liver, heart, kidney, lung, spleen, retina, bone, lymph node, endocrine gland, reproductive organ, blood, nerve, vascular tissue, and olfactory epithelium. In yet another preferred embodiment, the RNA may be isolated from a cell or tissue source selected from the group consisting of embryonic and tumorigenic.

In a preferred embodiment, the present invention may provide a proportionally amplified nucleic acid preparation comprising RNA obtained by the described methods. In another preferred embodiment, the present invention may also provide a proportionally amplified nucleic acid preparation comprising DNA obtained by the described methods.

The present invention preferably provides a gene expression monitoring system comprising a solid support, which comprises nucleic acid probes, and the proportionally amplified nucleic acid preparations. In a preferred embodiment, the present invention may provide a nucleic acid detection system comprising the proportionally amplified nucleic acid preparations immobilized to a solid support.

Other objectives, features, and advantages of the present invention will become apparent from the following detailed description. The detailed description and the specific examples, while indicating preferred embodiments of the invention, are provided by way of illustration only. Accordingly, the present invention also includes those various changes and modifications within the spirit and scope of the invention that may become apparent to those skilled in the art from this detailed description.

DETAILED DESCRIPTION OF THE PREFERRED EMBODIMENTS

Figure 1:
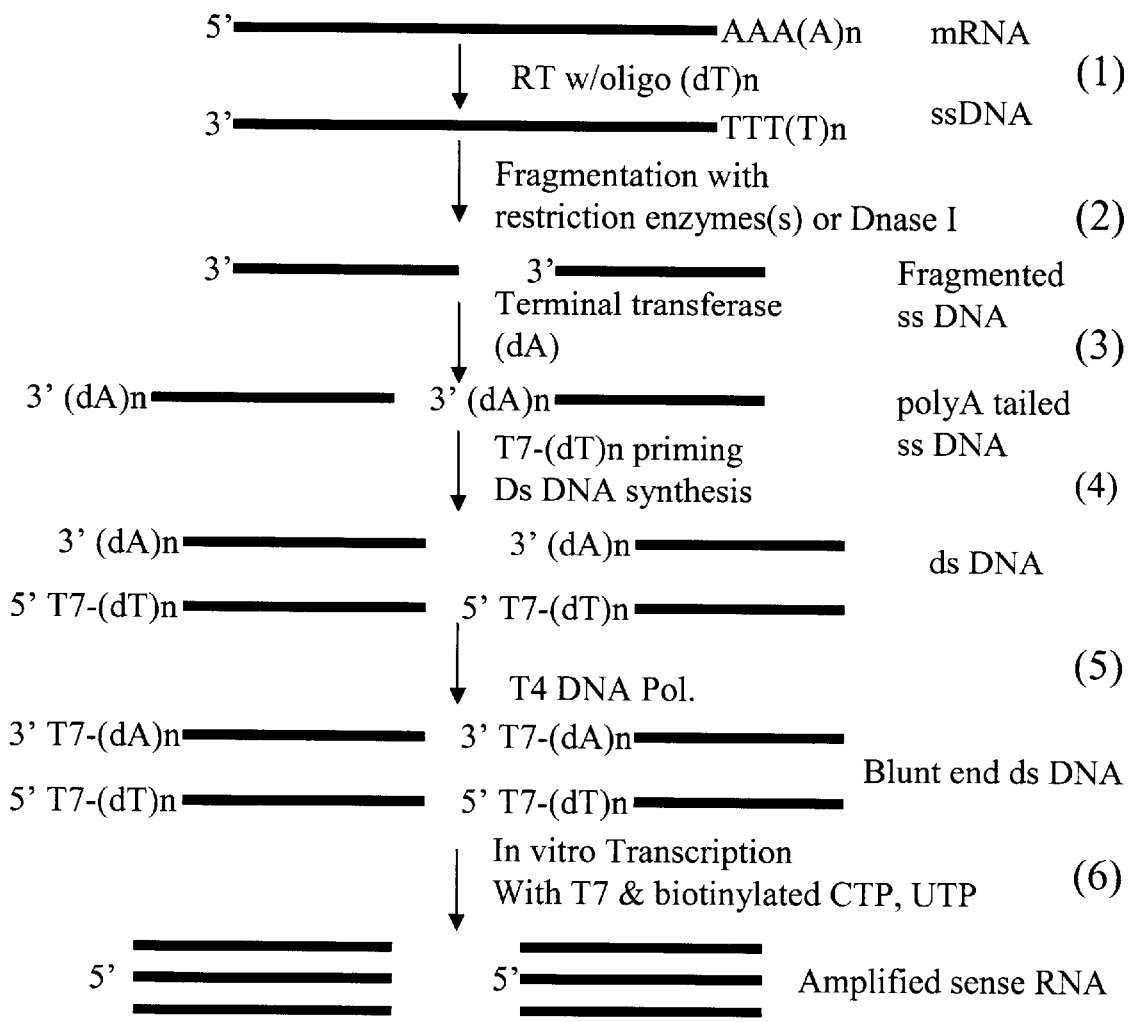
FIG. 1 depicts an overview of a preferred embodiment of the proportional amplification methods of the present invention. Single-stranded cDNA may be produced from total RNA containing a poly(A)+ mRNA template in the presence of reverse transcriptase, oligo-dT primer(s), and deoxynucleotide triphosphates (dNTPs) (1). Fragments of the single-stranded cDNA can be created, preferably with any enzyme capable of cleaving single-stranded DNA (such as DNase I or HaeIII), or by physical methods such as sonication or shearing (2). Terminal transferase may be used to transfer a poly(A) or poly(G) sequence to the 3'-termini of the single-stranded cDNA fragments (3). An oligonucleotide primer, which preferably includes a poly(T) or poly(C) region and a consensus sequence for the T7 RNA polymerase promoter, may be applied to the poly(A) or poly(G) tailed single-stranded cDNA fragments, and second strand DNA synthesis may proceed to yield double-stranded cDNA (4). T4 DNA polymerase may be used preferably to produce blunt ends in the presence of the appropriate dNTPs (5). In vitro transcription of the double-stranded cDNA, preferably with T7 RNA polymerase in the presence of biotinylated, fluorescently labeled, or radiolabeled CTP or UTP, can produce labeled, amplified sense RNA (6).
Figure 2:
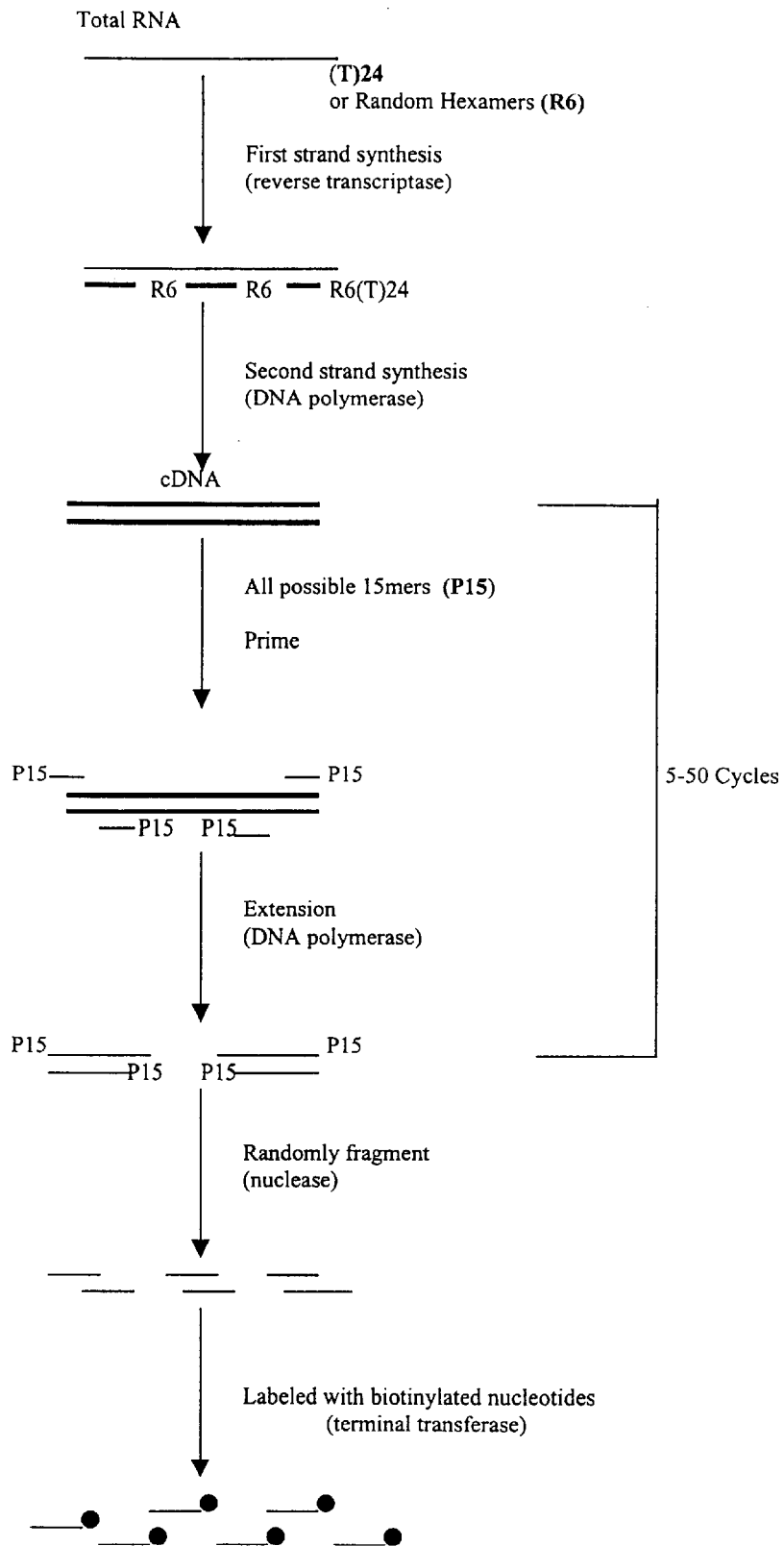
FIG. 2 depicts an overview of another preferred embodiment of the proportional amplification methods of the present invention. Double-stranded cDNA may be produced from total RNA. In the alternative, single-stranded cDNA may be used. The cDNA may be amplified with random primer extension, and the PCR products purified to remove residual primers.
Figure 3:
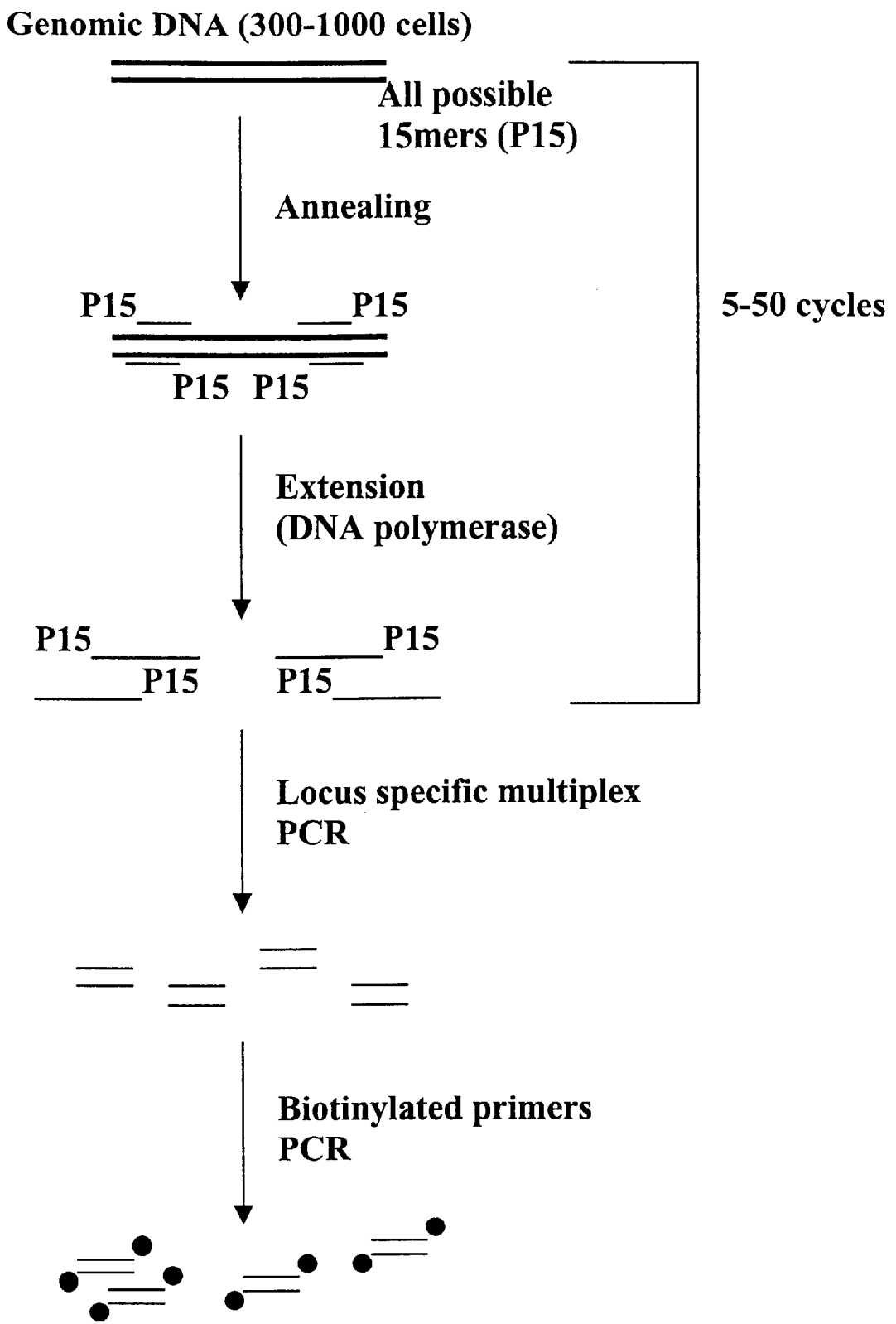
FIG. 3 depicts an overview of another preferred embodiment of the proportional amplification methods of the present invention. Double-stranded cDNA may be produced from genomic DNA or total RNA. The cDNA may be amplified by locus specific multiplex PCR directed to single nucleotide polymorphism (SNP) markers.
Figure 4:
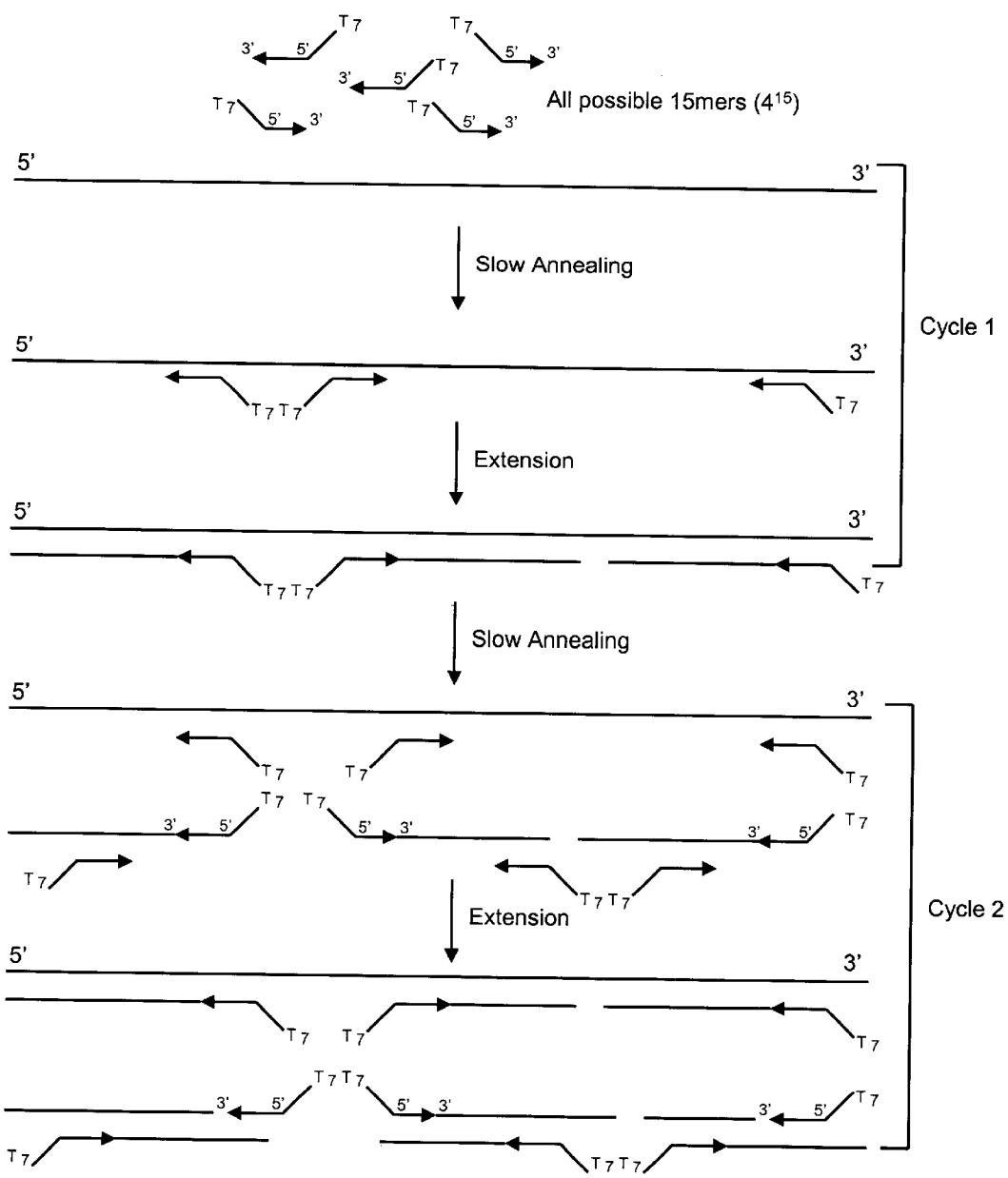
FIG. 4 depicts an overview of another preferred embodiment of the proportional amplification methods of the present invention. In this method, a common T7 promoter sequence (or any other common sequence) may be attached to the 5' end of the random primers. All the fragments generated by the random primer extension reaction can contain the common T7 promoter sequences. The products of the random primer extension reaction can be further amplified by the T7 promoter sequence (or any other common sequence) through PCR or in vitro transcription reaction by T7 polymerase.
Figure 5:
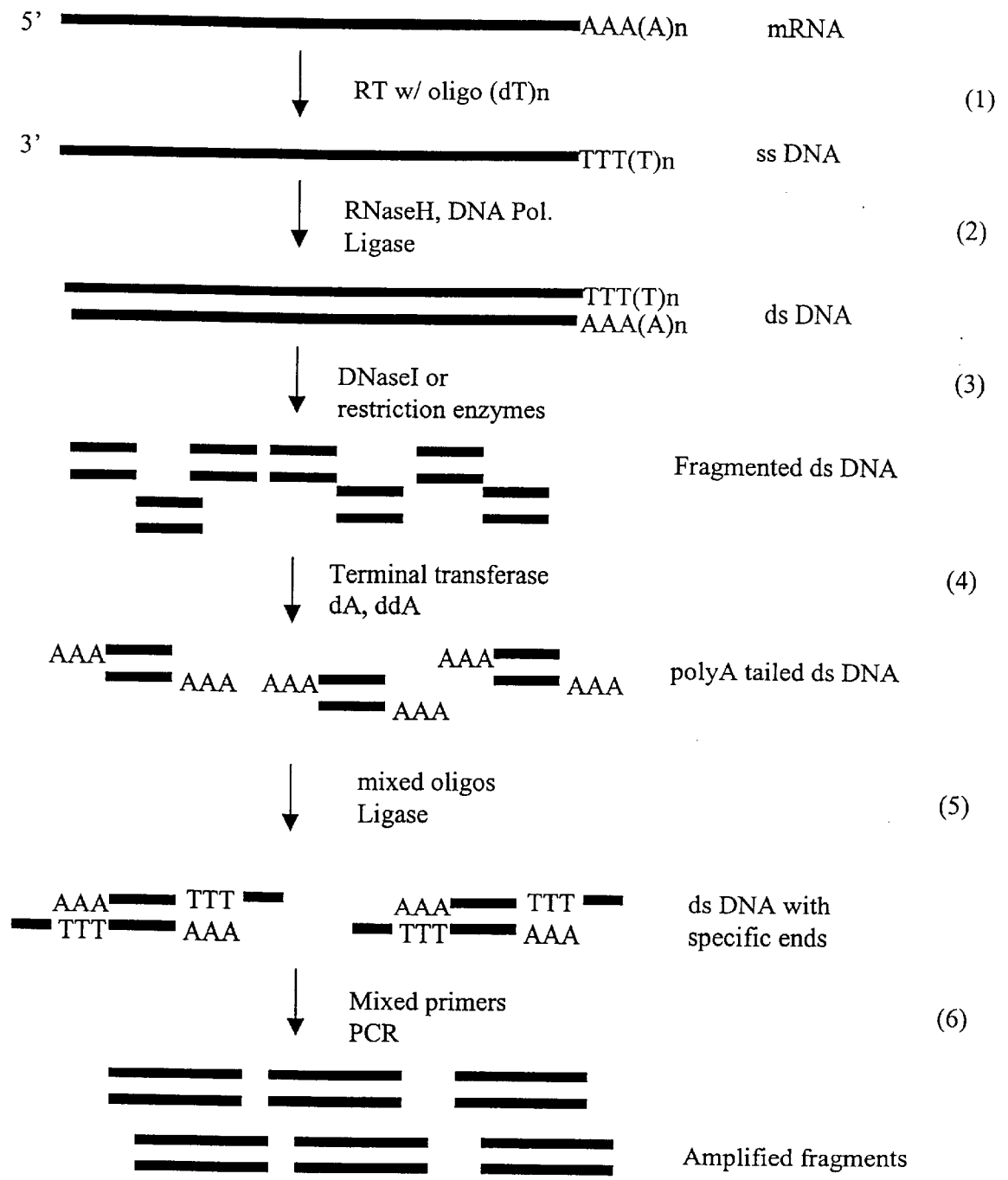
FIG. 5 depicts an overview of yet another preferred embodiment of the proportional amplification methods of the present invention. Single-stranded cDNA may be produced from a poly(A)+ mRNA template in the presence of reverse transcriptase, oligo-dT primer(s), and deoxynucleotide triphosphates (dNTPs) (1). Double-stranded DNA may be produced from the single-stranded DNA in the presence of RNaseH, DNA polymerase and DNA ligase (2). Fragments of the double-stranded DNA can be created, preferably with any enzyme capable of cleaving double stranded DNA, or by physical methods such as sonication or shearing (3). Terminal transferase may be used to transfer a poly(A) or poly(G) sequence to the 3'-termini of the double-stranded DNA fragments (4). An oligonucleotide primer, which preferably includes a poly(T) or poly(C) region (and optionally a consensus sequence for the T7 RNA polymerase promoter) (5), may be introduced to the poly(A) or poly(G) tailed double-stranded DNA fragments, and PCR initiated (6). Labeling can occur during PCR by using biotin-labeled primers or by incorporating biotinylated dNTPs. In the alternative, PCR products may be labeled afterwards with biotinylated ddUTP or ddCTP. Where a consensus sequence for the T7 RNA polymerase promoter was incorporated, in vitro transcription may occur to allow additional amplification up to several hundred fold, while facilitating the retention of the relative abundance of each transcript in the original nucleic acid population.

Those skilled in the art will recognize that the products and methods embodied in the present invention may be applied to a variety of systems, including commercially available gene expression monitoring systems involving nucleic acid probe arrays, membrane blots, microwells, beads, and sample tubes, constructed with various materials using various methods known in the art. Accordingly, the present invention is not limited to any particular environment, and the following description of specific embodiments of the present invention are for illustrative purposes only.

In a preferred embodiment, the present invention can involve the proportional amplification of nucleic acids, which may comprise (A) creating fragments of a single-stranded DNA population, synthesizing double-stranded DNA from the fragments of a single-stranded DNA population, and producing multiple copies of sense RNA from the double-stranded DNA; or (B) creating fragments of a double-stranded DNA population, and synthesizing multiple copies of the fragments of a double-stranded DNA population; or (C) synthesizing multiple copies of a double-stranded DNA population, and creating fragments of the multiple copies of a double-stranded DNA population.

Nucleic acids according to the present invention may include any polymer or oligomer of pyrimidine and purine bases, preferably cytosine, thymine, and uracil, and adenine and guanine, respectively. See Albert L. Lehninger, PRINCIPLES OF BIOCHEMISTRY, at 793–800 (Worth Pub. 1982). Indeed, the present invention contemplates any deoxyribonucleotide or ribonucleotide component, and any chemical variants thereof, such as methylated, hydroxymethylated or glucosylated forms of these bases, and the like. The polymers or oligomers may be heterogeneous or homogeneous in composition, and may be isolated from naturally-occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

The single-stranded or double-stranded DNA populations according to the present invention may refer to any mixture of two or more distinct species of single-stranded DNA or double-stranded DNA, which may include DNA representing genomic DNA, genes, gene fragments, oligonucleotides, PCR products, expressed sequence tags (ESTs), or nucleotide sequences corresponding to known or suspected single nucleotide polymorphisms (SNPs), having nucleotide sequences that may overlap in part or not at all when compared to one another. The species may be distinct based on any chemical or biological differences, including differences in base composition, order, length, or conformation. The single-stranded DNA population may be isolated or produced according to methods known in the art, and may include single-stranded cDNA produced from a MRNA template, single-stranded DNA isolated from double-stranded DNA, or single-stranded DNA synthesized as an oligonucleotide. The double-stranded DNA population may also be isolated according to methods known in the art, such as PCR, reverse transcription, and the like.

Where the nucleic acid sample contains RNA, the RNA may be total RNA, poly(A)+ RNA, mRNA, rRNA, or tRNA, and may be isolated according to methods known in the art. See, e.g, T. Maniatis et al., MOLECULAR CLONING: A LABORATORY MANUAL, 188–209 (Cold Spring Harbor Lab., Cold Spring Harbor, N.Y. 1982). The RNA may be heterogeneous, referring to any mixture of two or more distinct species of RNA. The species may be distinct based on any chemical or biological differences, including differences in base composition, length, or conformation. The RNA may contain full length mRNAs or MRNA fragments (i.e., less than full length) resulting from in vivo, in situ, or in vitro transcriptional events involving corresponding genes, gene fragments, or other DNA templates. In a preferred embodiment, the mRNA population of the present invention may contain single-stranded poly(A)+ RNA, which may be obtained from a RNA mixture (e.g., a whole cell RNA preparation), for example, by affinity chromatography purification through an oligo-dT cellulose column.

Where the single-stranded DNA population of the present invention is cDNA produced from a mRNA population, it may be produced according to methods known in the art. See, e.g, Maniatis et al., supra, at 213–46. In a preferred embodiment, a sample population of single-stranded poly(A)+ RNA may be used to produce corresponding cDNA in the presence of reverse transcriptase, oligo-dT primer(s) and dNTPs. Reverse transcriptase may be any enzyme that is capable of synthesizing a corresponding cDNA from an RNA template in the presence of the appropriate primers and nucleoside triphosphates. In a preferred embodiment, the reverse transcriptase may be from avian myeloblastosis virus (AMV), Moloney murine leukemia virus (MMULV) or Rous Sarcoma Virus (RSV), for example, and may be thermal stable enzyme (e.g., hTth DNA polymerase).

In a preferred embodiment of the present invention, the single-stranded cDNA produced using a MRNA population as template may be isolated from any resulting RNA:DNA heteroduplexes by heat or enzyme treatment (e.g., RNase H). Fragments of the single-stranded cDNA population may be created by treatment with any enzyme capable of cleaving single-stranded DNA. Examples of such enzymes may include some restriction enzymes (e.g., HaeIII), DNase I, or the like, and the digestion conditions (e.g., time and enzyme concentration) may be regulated to achieve the desired amount and type of fragmentation. Fragments of the single-stranded cDNA population may also be created by physical methods such as sonication or shearing. In addition, fragments of the single-stranded cDNA population may be produced by fragmentation of double-stranded DNA followed by denaturation to obtain single-stranded DNA.

Fragmentation of double-stranded DNA or RNA may occur by enzymatic treatment or physical methods. According to the present invention, the length of the fragments of the single-stranded DNA, double-stranded DNA, or RNA, are preferably from about 30 nucleotides to about 3,000 nucleotides in length, more preferably, from about 30 nucleotides to about 750 nucleotides in length, and even more preferably, from about 30 nucleotides to about 150 nucleotides in length.

The creation of fragments of the single-stranded DNA, double-stranded DNA, or RNA population can facilitate a substantial reduction in amplification bias. For example, by making amplified sense RNA from fragments of the single-stranded cDNA produced from a RNA population according to the present invention, the resulting amplified sense RNA population can contain transcripts, which in combination can span the entire length of each RNA species included in the original sample population. In so doing, amplification bias for shorter length transcripts or against certain sequences may be ameliorated by averaging results obtained with respect to a particular RNA species. Because each region of each RNA is represented by multiple fragments of the amplified sense RNA, the entire sequence of the individual MRNA in the original RNA sample population may be amplified without overall bias. Similarly, where restriction enzyme fragmentation is employed, the reaction products of the same sample with different restriction enzymes may be pooled to facilitate the achievement of an unbiased amplification.

In a preferred embodiment, terminal transferase may be used to add poly(A) or poly(G) sequences to the 3'-termini of the single-stranded DNA fragments. The double-stranded DNA of the present invention may be synthesized from the heterogeneous single-stranded DNA fragments.

An oligonucleotide primer may be applied to the poly(A), poly(G), poly(C) or poly (T) tailed heterogeneous single-stranded DNA fragments. The oligonucleotide primer preferably includes a poly(T) or poly(C) region complementary to the poly(A) or poly(G) tail attached to the single-stranded DNA fragments. In addition, the oligonucleotide primer preferably includes a promoter consensus sequence capable of facilitating transcription by the RNA polymerase used, for example, the DNA-directed RNA polymerases derived from bacteriophage T7, T3 or SP6. The oligonucleotide primer may be synthesized, for example, using a PCR-MATE Model 391 DNA synthesizer (Applied Biosystems) and purified by high-performance liquid chromatography before use. Second strand DNA synthesis may occur to yield the double-stranded DNA. See, e.g., Examples, infra.

In a preferred embodiment of the present invention, the ends of the double-stranded DNA may be blunted to prevent any concatenation of the double-stranded DNA fragments. T4 DNA polymerase or *Escherichia coli* DNA polymerase I (Klenow fragment), for example, may be used preferably to produce blunt ends in the presence of the appropriate dNTPs.

In another preferred embodiment, multiple copies of the DNA fragments may be obtained according to PCR methods known in the art in the presence of the appropriate primers. See R. K. Saiki et al., Science 220:1350–1354 (1985). In such circumstances, PCR cycles may preferably be limited to less than twenty to minimize amplification bias.

Multiple copies of sense RNA according to the present invention may be obtained by in vitro transcription from the DNA fragments preferably using T7 RNA polymerase in the presence of the appropriate nucleoside triphosphates.

In a preferred embodiment of the present invention, the multiple copies of sense RNA may be labeled by the incorporation of biotinylated, fluorescently labeled or radiolabeled CTP or UTP during the RNA synthesis. Alternatively, labeling of the multiple copies of sense RNA may occur following the RNA synthesis via the attachment of a detectable label in the presence of terminal transferase. In a preferred embodiment of the present invention, the detectable label may be radioactive, fluorometric, enzymatic, or colorimetric, or a substrate for detection (e.g., biotin). Other detection methods, involving characteristics such as scattering, IR, polarization, mass, and charge changes, may also be within the scope of the present invention.

In a preferred embodiment of the present invention, shorter fragments of the proportionally amplified sense RNA may be created in the presence of heat and $Mg^{++}$. The fragments of the multiple copies of DNA or sense RNA may preferably be from about 30 nucleotides to about 150 nucleotides in length. In a preferred embodiment, the fragments of the proportionally amplified DNA or sense RNA of the present invention may be analyzed with a system involving the detection of the presence or absence of hybridization of the fragments of the proportionally amplified DNA or sense RNA to discrete oligonucleotides or cDNAs, arranged in an array or otherwise. In such circumstances, short fragments of the proportionally amplified DNA or sense RNA may facilitate hybridization. Indeed, the proportional amplification methods of the present invention, which preferably result in fragments of multiple copies of DNA or sense RNA, may yield unexpected (or better) results with respect to gene expression monitoring or nucleic acid detection versus DNA or RNA obtained by existing amplification methods, possibly because of differences in conformation or other molecular interaction.

The foregoing methods of the present invention may preferably be repeated one or more times to produce an additional set(s) of proportionally amplified DNA or sense RNA from an original sample nucleic acid population. Therefore, all references to an additional set according to the invention may include two or more total cycles achieved by the methods of the present invention.

In a preferred embodiment, the proportionally amplified DNA or sense RNA of the present invention may be analyzed with a gene expression monitoring system. Several such systems are known. See, e.g., U.S. Pat. No. 5,677,195; Lisa Wodicka et al., *Nature Biotechnology* 15:1359–1367 (1997); David J. Lockhart et al., *Nature Biotechnology* 14:1675–1680 (1996). A gene expression monitoring system according to the present invention may be a nucleic acid probe array such as the GeneChip® nucleic acid probe array (Affymetrix, Santa Clara, Calif.). A nucleic acid probe array preferably comprises nucleic acids bound to a substrate in known locations. In other embodiments, the system may include a solid support or substrate, such as a membrane, filter, microscope slide, microwell, sample tube, bead, bead array, or the like. The solid support may be made of various materials, including paper, cellulose, nylon, polystyrene, polycarbonate, plastics, glass, ceramic, stainless steel, or the like. The solid support may preferably have a rigid or semi-rigid surface, and may preferably be spherical (e.g., bead) or substantially planar (e.g., flat surface) with appropriate wells, raised regions, etched trenches, or the like. The solid support may also include a gel or matrix in which nucleic acids may be embedded.

The gene expression monitoring system, in a preferred embodiment, may comprise a nucleic acid probe array (including an oligonucleotide array, a cDNA array, a spotted array, and the like), membrane blot (such as used in hybridization analysis such as Northern, Southern, dot, and the like), or microwells, sample tubes, beads or fibers (or any solid support comprising bound nucleic acids). See U.S. Pat. No. 5,770,722, U.S. Pat. No. 5,744,305, U.S. Pat. No. 5,677,195 and U.S. Pat. No. 5,445,934, which are incorporated here in their entirety by reference. See also Examples, infra. The gene expression monitoring system may also comprise nucleic acid probes in solution.

The gene expression monitoring system according to the present invention may be used to facilitate a comparative analysis of expression in different cells or tissues, different subpopulations of the same cells or tissues, different physiological states of the same cells or tissue, different developmental stages of the same cells or tissue, or different cell populations of the same tissue. In a preferred embodiment, the proportional amplification methods of the present invention can provide reproducible results (i.e., within statistically significant margins of error or degrees of confidence) sufficient to facilitate the measurement of quantitative as well as qualitative differences in the tested samples. The proportional amplification methods of the present invention may also facilitate the identification of single nucleotide polymorphisms (SNPs) (i.e., point mutations that can serve, for example, as markers in the study of genetically inherited diseases) and other genotyping methods from limited sources. See, e.g., Francis S. Collins et al., 282 SCIENCE 682 (1998). The mapping of SNPs can occur by any of various methods known in the art, one such method being described in U.S. Pat. No. 5,679,524, which is hereby incorporated by reference.

The RNA, single-stranded DNA, or double-stranded DNA population of the present invention may be obtained or derived from any tissue or cell source. Indeed, the nucleic acid sought to be amplified may be obtained from any biological or environmental source, including plant, viron, bacteria, fungi, or algae, from any sample, including body fluid or soil. In one embodiment, eukaryotic tissue is preferred, and in another, mammalian tissue is preferred, and in yet another, human tissue is preferred. The tissue or cell source may include a tissue biopsy sample, a cell sorted population, cell culture, or a single cell. In a preferred embodiment, the tissue source may include brain, liver, heart, kidney, lung, spleen, retina, bone, lymph node, endocrine gland, reproductive organ, blood, nerve, vascular tissue, and olfactory epithelium. In yet another preferred embodiment, the tissue or cell source may be embryonic or tumorigenic.

Tumorigenic tissue according to the present invention may include tissue associated with malignant and pre-neoplastic conditions, not limited to the following: acute lymphocytic leukemia, acute myelocytic leukemia, myeloblastic leukemia, promyelocytic leukemia, myelomonocytic leukemia, monocytic leukemia, erythroleukemia, chronic myelocytic (granulocytic) leukemia, chronic lymphocytic leukemia, polycythemia vera, lymphoma, Hodgkin's disease, non-Hodgkin's disease, multiple myeloma, Waldenstrom's macroglobulinemia, heavy chain disease, solid tumors, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma. See Fishman et al., Medicine, 2 d Ed. (J.B. Lippincott Co., Philadelphia, Pa. 1985).

In yet another preferred embodiment of the present invention, a nucleic acid detection system, the proportionally amplified DNA or sense RNA, or fragments thereof, may be immobilized directly or indirectly to a solid support or substrate by methods known in the art (e.g., by chemical or photoreactive interaction, or a combination thereof). The resulting immobilized sense RNA may be used as probes to detect nucleic acids in a sample population that can hybridize under desired stringency conditions. Such nucleic acids may include DNA contained in the clones and vectors of cDNA libraries.

Without further elaboration, one skilled in the art with the preceding description can utilize the present invention to its fullest extent. The following examples are illustrative only, and not intended to limit the remainder of the disclosure in any way.

EXAMPLE ONE

Amplified Sample Preparation
First Round of Amplification

Step 1: First strand DNA synthesis. Using Superscript Choice System (Life Technologies, Inc., Gaithersburg, Md., Catalog #18090), the RNA sample can be mixed with up to 10 $\mu$L $H_2O$ and 1 $\mu$L oligo(dT) 12–18 (0.5 ug/uL). The mixture can be incubated at 70° C. for 10 minutes, then chilled on ice. To this, may be added 4 $\mu$L 5×First Strand cDNA buffer, 2 $\mu$L 0.1M DTT, 1 $\mu$L 10 mM dNTP mix, and 2 $\mu$L Superscript II RT (200 U/$\mu$L) for a total volume of 20 $\mu$L. The mixture can be incubated at 42° C. for 1 hour.

Step 2: Fragmentation of Single-Stranded cDNA. The first strand synthesis reaction may be quickly spun down, heated at 95° C. for 5 minutes, spun down again, and put on ice. To this, may be added 159 $\mu$L DEPC $H_2O$, 20 $\mu$L 10×Buffer 2, and 1 $\mu$L HaeIII (10 U/$\mu$L) for a total volume of 200 $\mu$L. These components can be mixed, spun down, and incubated at 37° C. for 2 hours. Inactivation of the enzyme at 70° C. for 15 minutes may occur, followed by a phenol/chloroform extraction, precipitation with 20 $\mu$L 3M NaOAC and 500 $\mu$L 100% cold ethanol, and storage at −20° C. overnight.

Step 3: Tailing. The fragmented single strand cDNA may be dissolved into 36 $\mu$L DEPC-treated $H_2O$, to which can be added 10 $\mu$L 5×TrT (Terminal Transferase) buffer, 2.5 $\mu$L dATP (5 mM), and 1.5 $\mu$L TrT (15 U/$\mu$L), for a total volume of 50 $\mu$L. This mixture can be incubated at 37° C. for 20 minutes, inactivated at 65° C. for 10 minutes, and denatured at 95° C. for 10 minutes.

Step 4: Second strand cDNA synthesis. The tailing reaction (50 $\mu$L) may be mixed with 118 $\mu$L DEPC $H_2O$, 1 $\mu$L T7-oligo(dT) 24 (100 pmol), 20 $\mu$L 10×React 2 buffer, 2 $\mu$L BSA (10 mg/mL), 5 $\mu$L dNTPs (10 mM), and 2 $\mu$L Klenow DNA polymerase (4 U/$\mu$L), 2 $\mu$L T4 DNA polymerase (5 U/$\mu$L), for a total volume of 200 $\mu$L. This mixture may be incubated at 14° C. overnight, followed by phenol/chloroform extraction, and instant precipitation with 100 $\mu$L 7.5M $NH_4OAC$ and 500 $\mu$L 100% ethanol at room temperature for 30 minutes. The pellet can be washed with 0.5 mL of 80% ethanol, and centrifuged at maximum speed at room temperature for 5 minutes.

Step 5: Sense RNA synthesis (amplification). Using Ambion's T7 MEGAscript System (Catalog #1334), the following may be mixed at room temperature: 1.5 $\mu$L cDNA, 2 $\mu$L 10×T7 transcription buffer, 2 $\mu$L T7 10×ATP (75 mM), 2 $\mu$L T7 10×GTP (75 mM), 1.5 $\mu$L T7 10×CTP (75 mM), 1.5 $\mu$L T7 10×GTP (75 mM), 7.5 $\mu$L biotin CTP (10 mM), 7.5 $\mu$L biotin UTP (10 mM), 2 $\mu$L 10×T7 enzyme mix, followed by incubation at 37° C. for 4–6 hours.

Step 6: Clean-up amplified RNA. This step may be accomplished by using Rneasy spin columns from QIAGEN (Catalog #74103) according to the *Rneasy Protocol for RNA Clean-up* from the QIAGEN handbook.

Second Round of Amplification

Step 7: First strand cDNA synthesis. The amplified RNA may be resuspended in DEPC $H_2O$ to a total volume of 8 $\mu$L, to which can be added 4 $\mu$L 5×first strand buffer, 2 $\mu$L random primer (100 ng/μL), 1 μL dNTPs (10 mM), 2 μL DTT (100 mM), 1 μL RNAsin, and 2 μL Supercript II (200 U/μL) for a total volume of 20 μL. This mixture may be incubate at 42° C. for 1 hour.

Step 8: Second strand DNA synthesis. The first strand reaction may be heated at 95° C. for 5 minutes, quickly spun down and put on ice. To this, may be added 36 μL DEPC $H_2O$, 3 μL T7-oligo(dT) 24 (100 pmol), 5 μL 10×React 2 buffer, 0.5 μL BSA (10 mg/mL), 1.5 μL 10 mM dNTP mix, 2 μL T4 DNA polymerase (5 U/μL), and 2 μL Klenow DNA polymerase (4 U/μL), for a total volume of 50 μL. This mixture may be incubated at 14° C. overnight, followed by phenol/chloroform extraction, and instant precipitation with 100 μL 7.5M $NH_4OAC$ and 500 μL 100% ethanol at room temperature for 30 minutes. The pellet can be washed with 0.5 mL of 80% ethanol, and centrifuged at maximum speed at room temperature for 5 minutes.

Step 9: Sense RNA re-amplification. This step may be accomplished following the same protocol as set forth in Step 5.

Step 10: Clean-up amplified RNA. This step may be accomplished following the same protocol as set forth in Step 6.

EXAMPLE TWO

GeneChip® Analysis

GeneChip® nucleic acid probe arrays are manufactured using technology that combines photolithographic methods and combinatorial chemistry. In a preferred embodiment, over 280,000 different oligonucleotide probes are synthesized in a 1.28 cm×1.28 cm area on each array. Each probe type is located in a specific area on the probe array called a probe cell. Measuring approximately 24 μm×24 μm, each probe cell contains more than 107 copies of a given oligonucleotide probe.

Probe arrays are manufactured in a series of cycles. A glass substrate is coated with linkers containing photolabile protecting groups. Then, a mask is applied that exposes selected portions of the probe array to ultraviolet light. Illumination removes the photolabile protecting groups enabling selective nucleotide phosphoramidite addition only at the previously exposed sites. Next, a different mask is applied and the cycle of illumination and chemical coupling is performed again. By repeating this cycle, a specific set of oligonucleotide probes is synthesized, with each probe type in a known physical location. The completed probe arrays are packaged into cartridges.

During the laboratory procedure, biotin-labeled RNA fragments referred to as the RNA target are hybridized to the probe array. The hybridized probe array is stained with streptavidin phycoerythrin conjugate and scanned by the Hewlett-Packard (HP) GeneArray™ Scanner at the excitation wavelength of 488 nm. The amount of emitted light at 570 nm and above is proportional to the amount of bound labeled target at each location on the probe array.

Step 1: Target Preparation

A total RNA population is isolated from tissue or cells and reverse transcribed to produce cDNA. Then, in vitro transcription (IVT) produces biotin-labeled cRNA from the cDNA. The cRNA is fragmented before hybridization.

Step 2: Target Hybridization

After the biotin-labeled cRNA is fragmented, a hybridization cocktail is prepared, which includes labeled sample (0.05 μg/μL), probe array controls (1.5, 5, 25 and 100 pM respectively), herring sperm DNA (0.1 mg/mL), and BSA (0.5 mg/mL). A cleanup procedure is performed on the hybridization cocktail after which 200 μL is applied to the probe array through one of the septa in the array. It is then hybridized to the probes on the probe array during a 16-hour incubation at 45° C.

The hybridization protocol involves the following: (1) equilibrate probe array to room temperature immediately before use; (2) heat the sample(s) to 95° C. for 5 minutes in a heat block; (3) meanwhile, wet the array by filling it through one of the septa with 1×Hybridization Buffer (1M NaCl, 0.1M MES pH 6.7, 0.01% Triton X-100) using a micropipettor and appropriate tips; incubate the probe array at the hybridization temperature for 10 minutes with rotation; (5) after incubation at 95° C. (step #2 above), transfer the samples to a 45° C. heat block for 5 minutes; (5) spin samples at maximum speed in a microcentrifuge for 5 minutes to remove any insoluble material from the hybridization mixture; (6) remove the buffer solution from the probe array cartridge and fill with 200 μL of the clarified hybridization cocktail avoiding any insoluble matter in the 20 μL at the bottom of the tube; (7) place probe array in rotisserie box in 45° C. oven; load probe arrays in a balanced configuration around rotisserie axis; rotate at 60 rpm; and (8) hybridize for 16 to 40 hours.

Step 3: Probe Array Washing, Staining, and Fluidics Station Setup

Immediately following the hybridization, the hybridized probe array undergoes manual washing and staining, then washing on the fluidics station. The protocol involves the following: (1) remove the hybridization cocktail from the probe array and set it aside in a microcentrifuge tube; store on ice during the procedure or at −20° C. for long-term storage; (2) rinse the probe array by pipetting 200 μL 1×MES buffer pH 6.7 through one of the probe array septa; (3) fill the probe array septa with 200 μL 6×SSPE-T (300 mL of 20×SSPE and 500 μL of 10% Triton X 100 to 700 mL of water, final pH 7.6) and wash with 6×SSPE-T on the fluidics station with wash A cycle (10 cycles, drain and fill twice each cycle); (4) remove the 6×SSPE-T and rinse the probe array with 0.1×MES buffer pH 6.7 (0.1 M MES, 0.1 M NaCl and 0.01% Triton); (5) fill the probe array with 200 μL 0.1×MES and incubate at 45° C. on the rotisserie at 60 rpm for 30 minutes; and (6) remove the 0.1×MES, rinse the probe array with 1×MES in the probe array while preparing the stain.

Staining the probe array involves preparing Streptavidin Phycoerythrin (SAPE) stain solution. Stain should be stored in the dark and foil wrapped or kept in an amber tube at 4° C. Remove stain from refrigerator and tap the tube to mix well before preparing stain solution. The concentrated stain or diluted SAPE stain solution should not be frozen. The SAPE stain should be prepared immediately before use.

For each probe array to be stained, combine the following components to a total volume of 200 μL (1:100 dilution of SAPE, final concentration of 10 μg/mL): 188 μL 1×MES; 10 μL of 50 mg/mL acetylated BSA (final concentration of 2.5 mg/mL); and 2 μL of 1 mg/mL streptavidin phycoerythrin (SAPE).

Remove the 1×MES and apply the stain solution to the probe array. Incubate 15 minutes at 60 rpm at room temperature or 40° C.

Remove the stain and fill the probe array with 6×SSPE-T. Wash the probe ray with 6×SSPE-T on the fluidics station with wash A cycle.

The experiment parameters are preferably defined using commercially available GeneChip® software (Affymetrix, Santa Clara, Calif.) on a PC-compatible workstation with a Windows NT® operating system. The probe array type, sample description, and comments are entered in the software and saved with a unique experiment name.

The user protocol involves the following: (1) launch the software from the workstation and choose Experiment Info from the Run menu; alternatively, click the New Experiment icon on the GeneChip® software tool bar; the Experiment Information dialog box will appear allowing the experiment name to be defined along with several other parameters such as probe array type, sample description, and comments; (2) type in the experiment name; click on the box to the right of Probe Array type and select the probe array type from the drop-down list; experiment name and probe array type are required; complete as much of the other information as desired; the protocol information at the bottom of the dialog box will be imported to the experiment information dialog box after the hybridization and scan have been completed; (3) save the experiment by choosing Save; the name of the experiment will be used by the software to access the probe array type and data for the sample while it is being processed; data files generated for the sample will be automatically labeled to correspond to the experiment name; the Protocol section of the dialog box will be filled in by the software; and (4) close the Experiment Information dialog box.

The GeneChip® Fluidics Station 400 is preferably used to wash the probe arrays. It is operated using the GeneChip® software as follows: (1) choose Fluidics from the Run menu; alternatively, click the Start Protocol icon on the GeneChip® software tool bar; the Fluidics Station dialog box will appear with a drop-down list for the experiment name; a second list is accessed for the Protocol for each of the four fluidics station modules; (2) prime the fluidics station, by clicking Protocol in the Fluidics Station dialog box; choose Prime for the respective modules in the Protocol drop-down list; change the intake buffer reservoir A and B to 6×SSPE-T; click Run for each module to begin priming; priming should be done whenever the fluidics station is first started up, when wash solutions are changed, after washing if a shutdown has been performed on any module, and if the LCD window instructs the user to prime; priming ensures that the wash lines are filled with the appropriate buffer and the fluidics station is ready for washing; a prime takes approximately 3 to 5 minutes to complete; the fluidics station LCD window and the Fluidics Station dialog box will display the status of the prime and give instructions as it progresses; follow the instructions on the LCD window and dialog box; when priming is complete, the LCD window and dialog box will indicate that the fluidics station is ready to run a wash; (3) wash the probe array on the fluidics station, by customizing the HYBWASH protocol to create a wash of 10 cycles with 2 mixes per cycle with 6×SSPE-T at room temperature; in the Fluidics Station dialog box on the workstation, select the correct experiment name in the drop-down Experiment list; the probe array type will appear automatically; in the Protocol drop-down list, select the modified HYBWASH protocol created in step 1 to control the wash of the probe array; if a customized protocol is run, check the parameters of each of the protocols chosen to be sure they are appropriate for your experiment; this can be done in the Fluidics Protocol dialog box found by choosing Edit Protocol under the Tools menu; choose Run in the Fluidics Station dialog box to begin the wash; follow the instructions on the LCD window on the fluidics station; open the probe array holder by pressing down on the probe array lever to the Eject position; place the appropriate probe array into the probe array holder of the selected module and gently push up on the lever to engage it; the latch should be secure when the probe array holder is fully closed; a light click should be heard; engage the probe array holder lever by firmly pushing up on it to the Engage position; the Fluidics Station dialog box and the LCD window will display the status of the wash as it progresses; when the wash is complete, the LCD window will display EJECT CARTRIDGE; eject the probe array by pushing down firmly on the probe array lever; and (4) perform the cleanout procedure, by returning the probe array to the probe array holder; latch the probe array holder by gently pushing it up until a light click is heard; engage by firmly pushing up on the probe array lever to the Engage position; the fluidics station will drain the probe array and then fill it with a fresh volume of the last wash buffer used; when it is finished, if the LCD window displays EJECT CARTRIDGE again, remove the probe array and inspect it again for bubbles; if no bubbles are present, it is ready to scan; after ejecting the probe array from the probe array bolder, the LCD window will display ENGAGE WASHBLOCK; latch the probe array bolder by gently pushing it up and in until a light click is heard; engage the washblock by firmly pushing up on the probe array lever to the Engage position; the fluidics station will automatically perform a Cleanout procedure; the LCD window will indicate the progress of the Cleanout procedure; when the Cleanout procedure is complete, the LCD window should display Washing done, READY; if no other washes are to be performed, place wash lines into a bottle filled with deionized water; choose Shutdown for all modules from the drop-down Protocol list in the Fluidics Station dialog box; click the Run button for all modules; after Shutdown protocol is complete, flip the ON/OFF switch of the fluidics station to the OFF position; and scan the probe array.

Step 4: Probe Array Scan

Once the probe array has been hybridized, stained, and washed, it is scanned. Each workstation running the software can control one scanner. Each scan takes approximately 5 minutes, and two scans are recommended.

The scanner acquires an image of each of the hybridized 24 $\mu$m×24 $\mu$m probe cells. Each complete probe array image is stored in a separate data file that corresponds to its experiment name and is saved with a data image file (.dat) extension.

The scanner is also controlled by the GeneChip® software. The probe array is scanned after the wash protocols are complete. The probe array scan proceeds as follows: (1) choose Scanner from the Run menu; alternatively, click the Start Scan icon in the GeneChip® software tool bar; the Scanner dialog box will appear with a drop-down list of experiments that have not been run; a scrollable window will also be displayed showing previous scans; choose the experiment name that corresponds to the probe array to be scanned; a previously run experiment can also be chosen from the Previous Experiments list by double-clicking on the name desired; (2) check for the correct pixel value and wavelength of the laser beam; for a 24 $\mu$m×24 $\mu$m probe array with a phycoerythrin stain: Pixel value=3 $\mu$m, Wavelength=570 nm; (3) once the experiment has been selected, click the Start button; a dialog box will prompt the user to load a sample into the scanner; and (4) load the Probe Array into the HP GeneArray™ Scanner; open the sample door on the scanner and insert the probe array into the holder; do not force the probe array into the holder; close the sample door of the scanner; start the Scan, by clicking OK in the Start Scanner dialog box; the scanner will begin scanning the probe array and acquiring data; when Scan in Progress is chosen from the View menu, the probe array image will appear on the screen as the scan progresses.

Step 5: Data Analysis and Interpretation

Data is analyzed using GeneChip® software. In the Image window, a grid is automatically placed over the image of the scanned probe array to demarcate the probe cells. After grid alignment (the user may adjust the alignment if necessary), the mean intensity at each probe cell is calculated by the software. The intensity patterns are analyzed.

After scanning the probe array, the resulting image data created is stored on the hard drive of the GeneChip® workstation as a .dat file with the name of the scanned experiment. In the first step of the analysis, a grid is automatically placed over the .dat file so that it demarcates each probe cell. One of the probe array library files, the .cif file, indicates to the software what size of grid should be used. Confirm the alignment of the grid by zooming in on each of the four corners and the center of the image.

If the grid is not aligned correctly, adjust its alignment by placing the cursor on an outside edge or corner of the grid. The cursor image will change to a small double-headed arrow. The grid can then be moved using the arrow keys or by clicking and dragging its borders with the mouse.

Sample analysis occurs as follows: (1) choose Defaults from the Tools menu to access the Probe Array Call Settings tab dialog box; in the Defaults dialog box, click on the Probe Array Call Settings tab to display probe array calling algorithm choices; (2) highlight GeneChip® Expression and click the Modify button or double click the algorithm name; (3) in the Probe Array Call Settings dialog box, select the probe array type in the drop down list; for that probe array make sure the Use As Current Algorithm cheek box is selected; (4) click the OK button to apply your choices for the selected probe array type; (5) in the Defaults dialog box, click the OK button to apply your choices regarding parameters set by all of the tab dialog boxes in the window; (6) after confirming that the above parameters are correct, select the appropriate image to be analyzed; and (7) select Analysis from the Run menu or click the Run Analysis icon on the GeneChip® software tool bar; the software calculates the average intensity of each probe cell using the intensities of the pixels contained in the cell; pixels on the edges of each cell are not included, which prevents neighboring cell data from affecting a cells calculated average intensity; the calculated average intensity is assigned an X/Y-coordinate position, which corresponds to the cell's position on the array; this data is stored as a .cel file using the same name as the .exp and .dat files; the .cel file is an intermediate data file; the software then applies the selected probe array algorithm to determine expression levels for each gene; this is done with reference to the information contained in the .cdf file, the second library file for the probe array; the resulting analysis is automatically displayed as a .chp file in the Expression Analysis window of GeneChip® software; the .chp file has the same name as the .exp, .dat, and .cel files.

The specific embodiments described above do not limit the scope of the present invention in any way as they are single illustrations of individual aspects of the invention. Functionally equivalent methods and components are within the scope of the invention. The scope of the appended claims thus includes modifications that will become apparent to those skilled in the art from the foregoing description.

We claim:

1. A method for amplification of a population of nucleic acids comprising a population of RNA to reduce amplification bias, said method comprising performing the following steps in the following order:

synthesizing a single-stranded DNA population from said population of RNA;

fragmenting said single-stranded DNA population to produce a fragmented single-stranded DNA population;

synthesizing double-stranded DNA from said fragmented single-stranded DNA population; and producing multiple copies of sense RNA from said double-stranded DNA.

2. The method of claim 1, wherein said single-stranded DNA population is produced from a nucleic acid population selected from the group consisting of one or more of the following: genomic DNA, cDNA, total RNA, and poly(A)$^+$ RNA.

3. The method of claim 2, wherein said poly(A)$^+$ RNA is MRNA.

4. The method of claim 1, further comprising:

making fragments of said multiple copies of sense RNA.

5. The method of claim 4, further comprising:

contacting said fragments of said multiple copies of sense RNA with a solid support comprising nucleic acid probes.

6. The method of claim 5, further comprising:

detecting the presence or absence of hybridization of said fragments of said multiple copies of sense RNA to said nucleic acid probes on said solid support.

7. The method of claim 5, wherein said solid support comprising nucleic acid probes is selected from the group consisting of a nucleic acid probe array, a membrane blot, a microwell, and a bead.

8. The method of claim 1, further comprising:

creating an additional set of single-stranded DNA from said multiple copies of sense RNA;

synthesizing an additional set of double-stranded DNA from said additional set of single-stranded DNA; and producing an additional set of multiple copies of sense RNA from said additional set of double-stranded DNA.

9. The method of claim 1, wherein said fragments of a single-stranded DNA population are from about 30 nucleotides to about 3,000 nucleotides in length.

10. The method of claim 9, wherein said fragments of a single-stranded DNA population are from about 30 nucleotides to about 750 nucleotides in length.

11. The method of claim 10, wherein said fragments of a single-stranded DNA population are from about 30 nucleotides to about 150 nucleotides in length.

12. The method of claim 2, wherein said RNA is isolated from an eukaryotic cell or tissue.

13. The method of claim 12, wherein said eukaryotic cell or tissue is mammalian.

14. The method of claim 13, wherein said mammalian cell or tissue is human.

15. The method of claim 2, wherein said RNA is isolated from a source selected from the group consisting of dissected tissue, microdissected tissue, a tissue subregion, a tissue biopsy sample, a cell sorted population, a cell culture, and a single cell.

16. The method of claim 2, wherein said RNA is isolated from a cell or tissue source selected from the group consisting of brain, liver, heart, kidney, lung, spleen, retina, bone, lymph node, endocrine gland, reproductive organ, blood, nerve, vascular tissue, and olfactory epithelium.

17. The method of claim 2, wherein said RNA is isolated from a cell or tissue source selected from the group consisting of embryonic and tumorigenic.

18. A method for the amplification of nucleic acid wherein amplification bias is reduced, said method comprising performing the following steps in the following order:

contacting mRNA having a poly (A) tail with a first primer comprising poly d(T);

generating first strand cDNA from the mRNA by extending the first primer by reverse transcriptase;

fragmenting the first strand cDNA to produce single-stranded cDNA fragments;

adding a poly d(A) tail to the 3' end of the single-stranded cDNA fragments;

contacting the single-stranded cDNA fragments with a second primer comprising a T7 promoter sequence and poly d(T);

forming a double stranded DNA by extending the second primer;

forming a double stranded DNA promoter region by adding the appropriate reagents; and producing multiple copies of RNA from the double stranded DNA strand comprising the promoter region.

19. The method of claim 18, further comprising contacting said multiple copies of RNA with a solid support further comprising nucleic acid probes; and detecting the presence or absence of hybridization of said multiple copies of RNA to said nucleic acid probes on said solid support.

20. The method of claim 19, wherein said solid support is selected from the group consisting of a nucleic acid probe array, a membrane blot, a microwell, and a bead.

21. The method of claim 18 wherein said single stranded cDNA fragments are 30 to 750 nucleotides in length.

22. The method of claim 18 wherein said mRNA is isolated from an eukaryotic cell or tissue.

* * * * *